(12) United States Patent
Peng et al.

(10) Patent No.: US 11,636,601 B2
(45) Date of Patent: Apr. 25, 2023

(54) PROCESSING FUNDUS IMAGES USING MACHINE LEARNING MODELS

(71) Applicant: GOOGLE LLC, Mountain View, CA (US)

(72) Inventors: Lily Hao Yi Peng, Mountain View, CA (US); Dale R. Webster, San Mateo, CA (US); Philip Charles Nelson, San Jose, CA (US); Varun Gulshan, Chicago, IL (US); Marc Adlai Coram, Stanford, CA (US); Martin Christian Stumpe, Belmont, CA (US); Derek Janme Wu, Mountain View, CA (US); Arunachalam Narayanaswamy, Sunnyvale, CA (US); Avinash Vaidyanathan Varadarajan, Los Altos, CA (US); Katharine Blumer, Mountain View, CA (US); Yun Liu, Mountain View, CA (US); Ryan Poplin, Sunnyvale, CA (US)

(73) Assignee: Google LLC, Mountain View, CA (US)

(*) Notice: Subject to any disclaimer, the term of this patent is extended or adjusted under 35 U.S.C. 154(b) by 135 days.

(21) Appl. No.: 17/212,811

(22) Filed: Mar. 25, 2021

(65) Prior Publication Data
US 2021/0209762 A1 Jul. 8, 2021

Related U.S. Application Data

(63) Continuation of application No. 16/325,580, filed as application No. PCT/US2017/047639 on Aug. 18, 2017, now Pat. No. 10,970,841.
(Continued)

(51) Int. Cl.
*G06T 7/00* (2017.01)
*G16H 50/30* (2018.01)
(Continued)

(52) U.S. Cl.
CPC ......... *G06T 7/0016* (2013.01); *G06N 3/0445* (2013.01); *G06N 3/08* (2013.01);
(Continued)

(58) Field of Classification Search
CPC ......... G06T 7/0016; G06T 2207/20081; G06T 2207/30041; G06T 2207/10016;
(Continued)

(56) References Cited

U.S. PATENT DOCUMENTS

| | | | | |
|---|---|---|---|---|
| 2011/0091083 A1* | 4/2011 | Liu | ................ | G06T 7/0012 382/128 |
| 2012/0213423 A1* | 8/2012 | Xu | ................ | G06T 7/143 382/131 |

(Continued)

FOREIGN PATENT DOCUMENTS

| | | |
|---|---|---|
| CN | 103200420 A | 7/2013 |
| CN | 104921727 A | 9/2015 |

(Continued)

OTHER PUBLICATIONS

Pachiyappan et al., "Automated diagnosis of diabetic retinopathy and glaucoma using fundus and OCT image" Lipids inn Health and Disease, 2012, 10 pages.
(Continued)

*Primary Examiner* — Brenda C Bernardi
(74) *Attorney, Agent, or Firm* — Fish & Richardson P.C.

(57) ABSTRACT

Methods, systems, and apparatus, including computer programs encoded on computer storage media, for processing fundus images using fundus image processing machine learning models. One of the methods includes obtaining a model input comprising one or more fundus images, each fundus image being an image of a fundus of an eye of a patient; processing the model input using a fundus image processing machine learning model, wherein the fundus
(Continued)

image processing machine learning model is configured to process the model input comprising the one or more fundus image to generate a model output; and processing the model output to generate health analysis data.

17 Claims, 12 Drawing Sheets

Related U.S. Application Data

(60) Provisional application No. 62/376,860, filed on Aug. 18, 2016.

(51) Int. Cl.
  *G16H 50/20* (2018.01)
  *G06N 3/04* (2006.01)
  *G06N 3/08* (2006.01)
(52) U.S. Cl.
  CPC ............. *G16H 50/20* (2018.01); *G16H 50/30* (2018.01); *G01N 2800/164* (2013.01); *G01N 2800/168* (2013.01); *G06T 2207/10016* (2013.01); *G06T 2207/20076* (2013.01); *G06T 2207/20081* (2013.01); *G06T 2207/30041* (2013.01)
(58) Field of Classification Search
  CPC ........ G06T 2207/20076; G06N 3/0445; G06N 3/08; G16H 50/20; G01N 2800/164; G01N 2800/168
  See application file for complete search history.

(56) References Cited

U.S. PATENT DOCUMENTS

| | | | |
|---|---|---|---|
| 2012/0257164 A1* | 10/2012 | Zee | A61B 3/12 351/246 |
| 2015/0110368 A1 | 4/2015 | Solanki et al. | |
| 2016/0092721 A1 | 3/2016 | Kanagasingam et al. | |
| 2016/0100753 A1 | 4/2016 | Liu | |
| 2016/0100806 A1 | 4/2016 | Mwanza et al. | |
| 2016/0232324 A1* | 8/2016 | Liu | A61B 5/4842 |
| 2016/0235373 A1* | 8/2016 | Sharma | A61B 8/0891 |
| 2018/0235467 A1* | 8/2018 | Celenk | G06V 40/197 |
| 2019/0088359 A1* | 3/2019 | Moore | G06V 20/00 |
| 2020/0202527 A1* | 6/2020 | Choi | A61B 8/08 |

FOREIGN PATENT DOCUMENTS

| | | |
|---|---|---|
| CN | 105547310 A | 5/2016 |
| CN | 105559748 A | 5/2016 |
| EP | 2285266 | 2/2011 |
| WO | WO 2009139722 A1 | 11/2009 |
| WO | WO 2010/138645 | 12/2010 |
| WO | WO 2011059409 A1 | 5/2011 |
| WO | WO 2014/186838 | 11/2014 |

OTHER PUBLICATIONS

Pratt et al., "Convolutional Neural Networks for Diabetic Retinopathy" Procedia Computer Science, 2016, 6 pages.
Chen et al., "Glaucoma detection based on deep convolutional neural network," 2015 37th Annual International Conference of the IEEE Engineering in Medicine and Biology Society (EMBC), Aug. 2015, 715-718.
IN Office Action in Indian Application No. 201927010233, dated Mar. 9, 2021, 8 pages (with English translation).
JP Notice of Submission of Publications in Japanese Appln. No. 2019-508910, dated Jan. 27, 2020, 3 pages (with English translation).
JP Office Action in Japanese Application No. 2019-508910, dated Dec. 21, 2020, 9 pages (with English translation).
JP Office Action in Japanese Application No. 2019-508910, dated Jun. 25, 2020, 10 pages (with English translation).
KR Office Action in Korean Application No. 10-2019-7007602, dated Jun. 22, 2020, 16 pages (with English translation).
PCT International Preliminary Report on Patentability in International Appln. No. PCT/US2017/04763, dated Feb. 28, 2019, 17 pages.
PCT International Search Report and Written Opinion in International Appln. No. PCT/US2017/04763, dated Mar. 5, 2018, 26 pages.
Subhashini et al., "Sequence to Sequence—Video to Text," arXiv, Oct. 2015, 9 pages.
Szegedy et al., "Going Deeper with Convolutions," IEEE Conference on Computer Vision and Pattern Recognition, Jun. 2015, 9 pages.
Szegedy et al., "Inception-v4, Inception-ResNet and the Impact of Residual Connections on Learning," arXiv, Aug. 2016, 9 pages.
Third Party Observation in Japanese Application No. 2019-508910, dated Nov. 12, 2020, 8 pages (with English translation).
Verma et al., "Screening for diabetic retinopathy by non-ophthalmologists:an effective public health tool," Acta Opthalmologica, Jul. 2003, 5 pages.
Xu et al., "Show, Attend and Tell: Neural Image Caption Generation with Visual Attention," arXiv, Apr. 2016, 22 pages.
Yousefi et al., "Glaucoma Progression Detection Using Structural Retinal Nerve Fiber Layer Measurements and Functional Visual Field Points," IEEE Transactions on Biomedical Engineering, Apr. 2014, 61(4): 1143-1154.
Yue-Hei Ng et al., "Beyond short snippets: Deep networks for video classification," Proceedings of the IEEE Conference on Computer Vision and Pattern Recognition, Jun. 2015, 9 pages.
Zhou et al., "Simple Baseline for Visual Question Answering" arXiv, Dec. 2015, 7 pages.
JP Office Action in Japanese Application No. 2019-508910, dated Aug. 23, 2021, 9 pages (with English translation).
EP Office Action in European Appln. No. 17784047.7, dated Aug. 5, 2022, 14 pages.
Office Action in Chinese Appln. No. 201780055989.8, dated Nov. 28, 2022, 30 pages (with English Translation).
Pre-Grant Opposition against Indian Patent Application No. 201927010233, dated Dec. 29, 2022, 383 pages.

* cited by examiner

PROCESSING FUNDUS IMAGES USING MACHINE LEARNING MODELS

CROSS-REFERENCE TO RELATED APPLICATIONS

This application is a continuation of U.S. patent application Ser. No. 16/325,580 filed on Feb. 14, 2019, which is a U.S. National Phase Application of International Patent Application No. PCT/US2017/047639 filed on Aug. 18, 2017, which claims the benefit of U.S. Provisional Application No. 62/376,860 filed on Aug. 18, 2016, the contents of which are incorporated herein by reference in their entirety.

BACKGROUND

This specification relates to processing images using a machine learning model.

Machine learning models receive an input and generate an output, e.g., a predicted output, based on the received input. Some machine learning models are parametric models and generate the output based on the received input and on values of the parameters of the model.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

Some neural networks are recurrent neural networks. A recurrent neural network is a neural network that receives an input sequence and generates an output sequence from the input sequence. In particular, a recurrent neural network uses some or all of the internal state of the network after processing a previous input in the input sequence in generating an output from the current input in the input sequence.

SUMMARY

This specification generally describes a system that generates health analysis data for a patient by processing data that includes one or more fundus images of the patient using a fundus image processing machine learning model.

Particular embodiments of the subject matter described in this specification can be implemented so as to realize one or more of the following advantages. A health analysis system can effectively analyze the health of a patient using only one or more images of the fundus of the patient's eye and minimal or no other patient data. In particular, the health analysis system can effectively analyze the presence or the probable progression of a specific medical condition using the fundus images. Instead or in addition, the health analysis system can effectively predict which treatments or follow-up actions will be most effective in treating the medical condition. Instead or in addition, the health analysis system can accurately evaluate the risk of the patient for undesirable health events or accurately evaluate the overall health of the patient using the fundus images. Instead or in addition, the health analysis system can accurately predict values of a set of factors that contribute to a risk of a particular set of health events happening to the patient using the fundus images.

In some implementations, the system can present a user of the system with data that explains the basis for the predictions generated by the system, i.e., the portions of the fundus image that the machine learning model focused on to generate a particular prediction. In so doing, the system can allow a medical practitioner or other user to have insight into the prediction process.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification generally describes a system that can generate health analysis data for a patient from an input that includes one or more fundus images of the patient and, optionally, other patient data. A fundus image is a photograph of the fundus of one of the eyes of the patient. The fundus of an eye is the interior surface of the eye opposite the lens and includes, among other things, the retina and the optic disc.

Generally, to generate the health analysis data for a given patient, the system processes the one or more fundus images and, optionally, the other patient data using a fundus image processing machine learning model to generate a model output for the patient and then generates the health analysis data from the model output.

Figure 1:
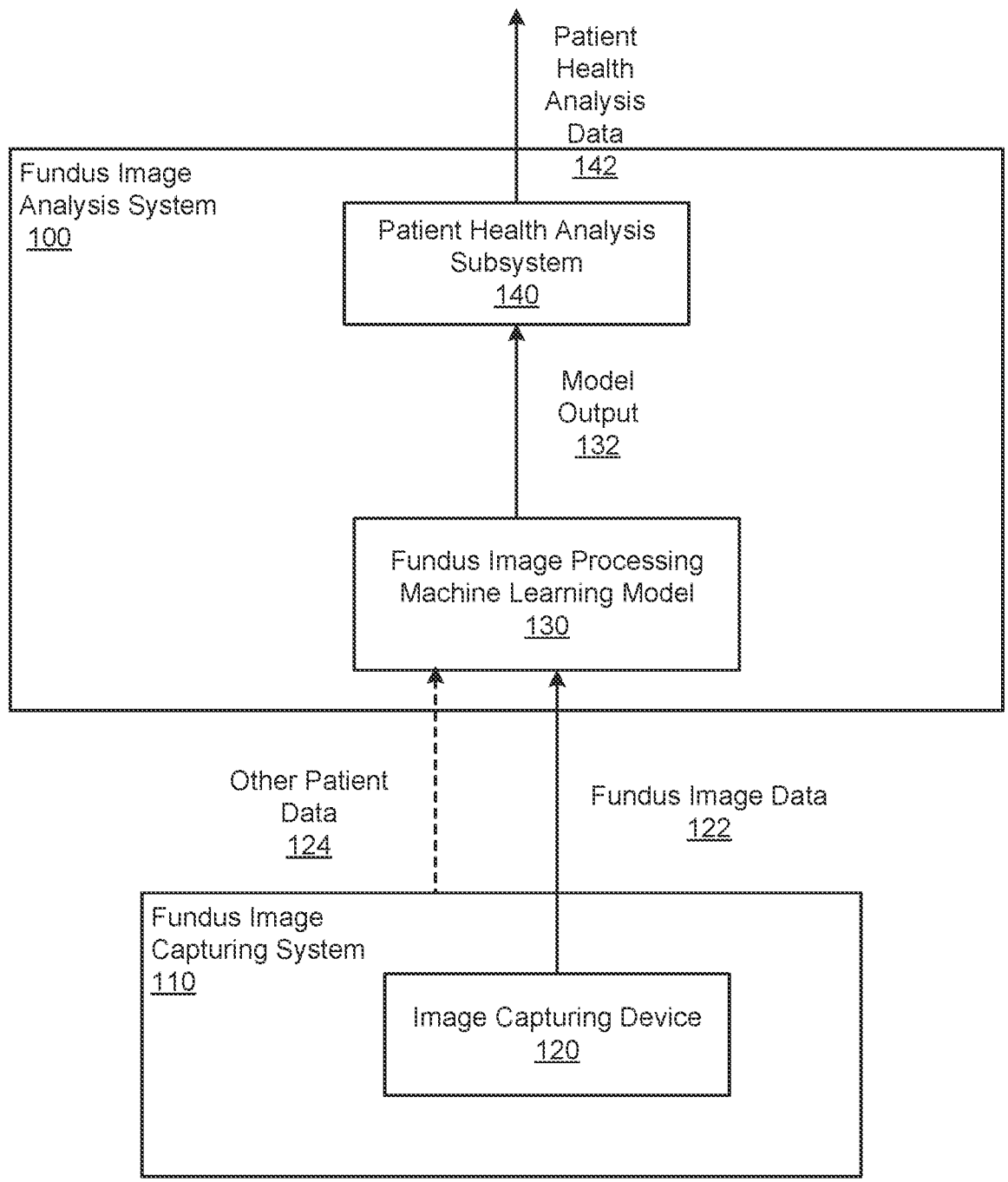
FIG. 1 shows an example fundus image analysis system.

FIG. 1 shows an example fundus image analysis system 100. The fundus image analysis system 100 is an example of a system implemented as computer programs on one or more computers in one or more locations, in which the systems, components, and techniques described below can be implemented.

For a given patient, the fundus image analysis system 100 receives fundus image data 122 that includes one or more fundus images of the patient's eye and generates health analysis data 142 that characterizes the health of the patient.

In some implementations, the fundus image analysis system 100 includes or is in communication with a fundus image capturing system 110 that generates the fundus images and provides them as input fundus image data 122 to the fundus image analysis system. In particular, the fundus image capturing system 110 includes one or more image capturing devices, e.g., an image capturing device 120, that are configured to capture images of the fundus of a patient. Generally, the image capturing device 120 is a specialized fundus camera that is configured to capture an appropriate type of fundus image, e.g., using color fundus photography, stereoscopic photography, wide field or ultra wide field photography, or scanning laser ophthalmoscopy (SLO). In some cases, the image capturing system 110 includes multiple image capturing devices that capture different types of fundus images.

In other implementations, the fundus image analysis system 100 receives the input fundus image data 122 from an external system, e.g., over a data communication network.

The fundus image analysis system 100 processes the input fundus image data 122 and, optionally, other data for the given patient using a fundus image processing machine learning model 130. The fundus image processing machine learning model 130 is a machine learning model that is configured to process the input fundus image data 122 and, optionally, other patient data 124 to generate a model output 132 that characterizes the health of the patient.

How many fundus images are in the fundus image data 122, whether the system 100 receives other patient data 124 and, if so, the nature of the other patient data 124 that is received, and the makeup of the model output 132 are dependent on the configuration of the fundus image processing machine learning model 130. Fundus image data, example configurations of the machine learning model 130, and example makeups of the model output 132 are described in more detail below with reference to FIGS. 2-9.

The fundus image analysis system 100 also includes a patient health analysis subsystem 140 that receives the model output 132 and generates the patient health analysis data 142. Generally, the patient health analysis subsystem 140 generates health analysis data that characterizes the model output in a way that can be presented to a user of the system. The patient health analysis subsystem 140 can then provide the health analysis data 142 for presentation to the user in a user interface, e.g., on a user computer of the patient or on a computer of a medical professional, store the health analysis data 142 for future use, or provide the health analysis data 142 for use for some other immediate purpose.

In some implementations, the fundus image analysis system 100 receives requests for patient health analysis data 142 from remote users of user computers over a data communication network. For example, a user computer, e.g., a computer on which the fundus image capturing system 110 is implemented, may be able to submit a request to the fundus image analysis system 100 over the data communication network by providing fundus image data as part of making an Application Programming Interface (API) call to the fundus image analysis system 100. In response to the API call, the fundus image analysis system 100 can generate the health analysis data 142 and transmit the health analysis data to the user computer over the data communication network.

Additionally, in some implementations, the machine learning model 130 is implemented by one or more computers that are remote from the fundus image analysis system 100. In these implementations, the fundus image analysis system 100 can access the machine learning model 130 by making an API call over a network that includes the input to the machine learning model 130 and can receive the model output 132 in response to the API call.

While the description in this specification generally describes a single machine learning model 130 that generates a particular model output, in some cases the system 100 includes or communicates with an ensemble of multiple machine learning models for a given kind of model output. Each machine learning model 130 generates the same kind of model output, and the system 100 or another system can combine the model outputs generated by the ensemble, e.g., by computing a measure of central tendency of the model outputs. The combined output can then be treated as the model output 132 by the system 100.

Figure 2A:
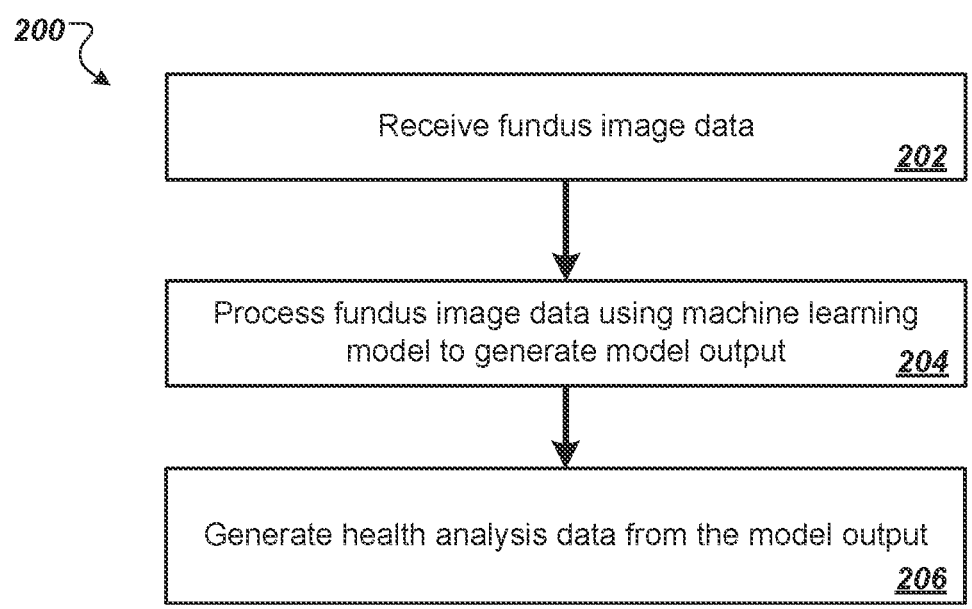
FIG. 2A is a flow diagram of an example process for generating health analysis data.

FIG. 2A is a flow diagram of an example process 200 for generating health analysis data. For convenience, the process 200 will be described as being performed by a system of one or more computers located in one or more locations. For example, a fundus image analysis system, e.g., the fundus image analysis system 100 of FIG. 1, appropriately programmed, can perform the process 200.

The system receives input fundus image data and, optionally, other patient data (step 202).

Generally, the fundus image data includes one or more fundus images of a patient's eye.

In some implementations, the fundus image data includes a single fundus image, e.g., an image that captures the current state of the patient's fundus.

In some other implementations, the fundus image data includes multiple fundus images that capture the current state of the patient's fundus. For example, the fundus image data can include one or more images of the fundus in the patient's left eye and one or more images of the fundus in the patient's right eye. As another example, the fundus images may include multiple different types of fundus photographs. For example, the fundus images may include two or more of: a color fundus photograph, a stereoscopic fundus photograph, a wide field or ultra wide field fundus photograph, or a scanning laser ophthalmoscopy (SLO) fundus photograph. As yet another example, the fundus images can include multiple images captured using different imaging technology, e.g., optical coherence tomography (OCT) and Heidelberg retinal tomography (HRT).

In yet other implementations, the fundus image data includes a temporal sequence of fundus images that capture how the state of the fundus has evolved over time. That is, the temporal sequence includes multiple fundus images, with each fundus image having been taken at a different time. In some implementations, the fundus images are ordered in the temporal sequence from least recent to most recent.

The other patient data is data that characterizes the patient's eye, data that generally characterizes the patient, or both. For example, the other patient data can include ocular measurement data, e.g., eye pressures, visual fields, visual acuity, central corneal thickness, and so on, patient demographics, e.g., age, gender, ethnicity, family history, and so on, or both.

The system processes the input fundus image data and, optionally, the other patient data using a fundus image processing machine learning model to generate a model output (step 204).

Optionally, prior to processing the fundus image data using the machine learning model, the system can pre-process the fundus images. For example, for a given image, the system can apply any of a variety of conventional image processing techniques to the image to improve the quality of the output generated by the machine learning model. As an example, the system may crop, scale, deskew or re-center the image. As another example, the system can remove distortion from the image, e.g., to remove blurring or to re-focus the image, using conventional image processing techniques.

In implementations where the fundus image data includes a single fundus image, the fundus image processing machine learning model is a feedforward machine learning model that has been configured by being trained on appropriately labeled training data to process the fundus image data and, optionally, the other patient data to generate a model output that characterizes a particular aspect of the patient's health. For example, the fundus image processing machine learning model may be a deep convolutional neural network. An example of a deep convolutional neural network that can be trained to process a fundus image to generate the model outputs described in this specification is described in Szegedy, Christian et al. "Going deeper with convolutions." Proceedings of the IEEE Conference on Computer Vision and Pattern Recognition, 2015. Other examples of deep convolutional neural networks, including convolutional neural networks with residual connections, that can be trained to process a fundus image to generate the model outputs described in this specification are described in Szegedy, Christian, et al. "Inception-v4, Inception-ResNet and the Impact of Residual Connections on Learning," available at http://arxiv.org/abs/1602.07261.

In implementations where the fundus image data includes multiple fundus images that characterize the current state of the patient's fundus, the fundus image processing machine learning model may be a feedforward fundus image processing machine learning model that has been configured by being trained on appropriately labeled training data to process all of the fundus images to generate a model output that characterizes a particular aspect of the patient's health. For example, the fundus image processing machine learning model may be a deep convolutional neural network that includes multiple towers of convolutional layers. An example of a deep convolutional neural network that can be trained to process multiple fundus images to generate the model outputs described in this specification is described in Yue-Hei Ng, Joe, et al. "Beyond short snippets: Deep networks for video classification," Proceedings of the IEEE Conference on Computer Vision and Pattern Recognition, 2015.

In implementations where the fundus image data includes a temporal sequence of fundus images, the fundus image processing machine learning model may be a recurrent fundus image processing machine learning model that has been configured to process each image in the temporal sequence one by one to, for each image, update the internal state of the recurrent fundus image processing machine learning model, and to, after the last image in the temporal sequence has been processed, generate a model output that characterizes a particular aspect of the patient's health. For example, the fundus image processing machine learning model may be a recurrent neural network that includes one or more long short-term memory (LSTM) layers. A recurrent neural network that can be trained to process a sequence of fundus images to generate the model outputs described in this specification is described in Venugopalan, Subhashini, et al. "Sequence to sequence-video to text." Proceedings of the IEEE International Conference on Computer Vision, 2015.

In some implementations, the model output is specific to a particular medical condition. Model outputs that are specific to a particular medical condition are described in more detail below with reference to FIGS. 3-6.

In some other implementations, the model output is a prediction of a future state of the fundus of the patient's eye. A model output that is a prediction of the future state of a fundus is described in more detail below with reference to FIG. 7.

In yet other implementations, the model output is a prediction of the risk of a particular health event occurring in the future. A model output that is a prediction of the risk of a particular event occurring is described in more detail below with reference to FIG. 8.

In yet other implementations, the model output characterizes the overall health of the patient. A model output that characterizes the overall health of the patient is described in more detail below with reference to FIG. 9.

In yet other implementations, the model output is a prediction of values of factors that contribute to a particular kind of health-related risk. A model output that is a prediction of values of risk factors is described in more detail below with reference to FIG. 10.

The system generates health analysis data from the model output (step 206). Generally, the health analysis data characterizes the model output in a way that can be presented to a user of the system.

In some implementations, the health analysis data also includes data derived from an intermediate output of the machine learning model that explains the portions of the fundus image or images that the machine learning model focused on when generating the model output. In particular, in some implementations, the machine learning model includes an attention mechanism that assigns respective attention weights to each of multiple regions of an input fundus image and then attends to features extracted from those regions in accordance with the attention weights. In these implementations, the system can generate data that identifies the attention weights and include the generated data as part of the health analysis data. For example, the generated data can be an attention map of the fundus image that reflects the attention weights assigned to the regions of the image. For example, the attention map can be overlaid over the fundus image to identify the areas of the patient's fundus that the machine learning model focused on when generating the model output. Generating data that identifies areas of the fundus that were focused on by the machine learning model is described in more detail below with reference to FIG. 11.

The system can then provide the health analysis data for presentation to the user in a user interface, e.g., on a user computer of the patient or on a computer of a medical professional, or store the health analysis data for future use.

Figure 2B:
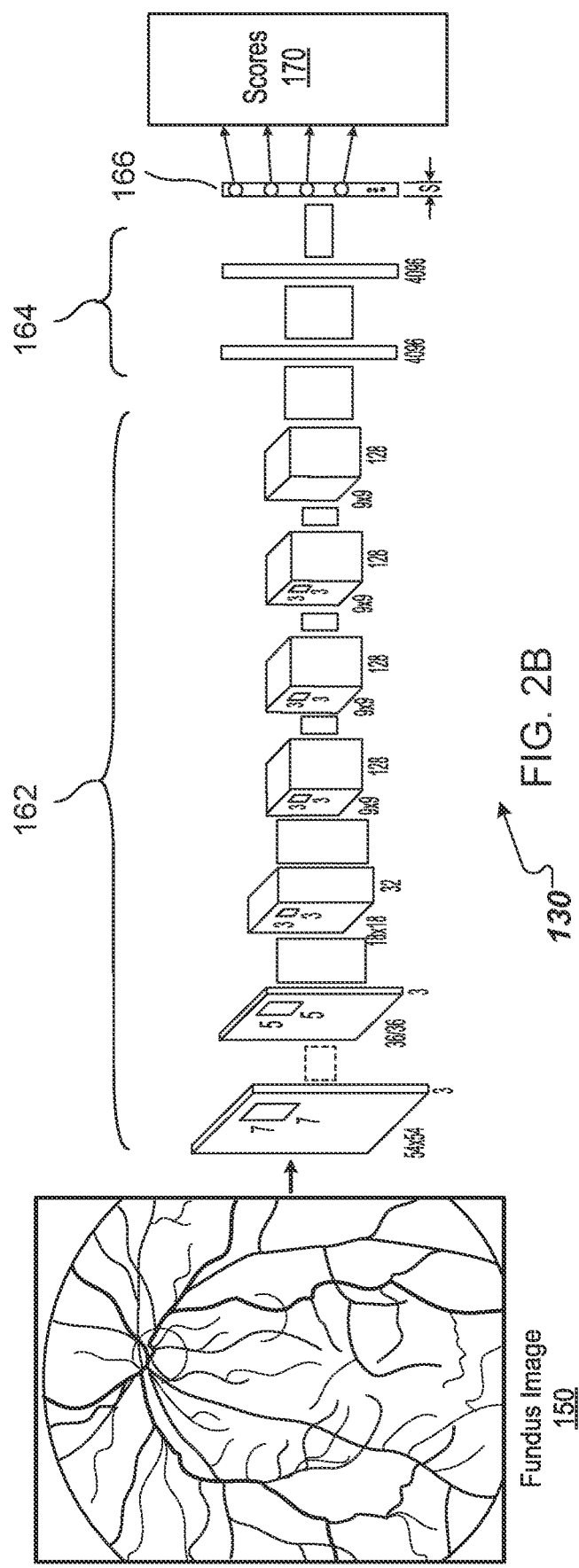
FIG. 2B shows the processing of an example fundus image by the fundus image processing machine learning model.

FIG. 2B shows the processing of an example fundus image 150 by the fundus image processing machine learning model 130. In particular, in the example of FIG. 1B, the fundus image processing machine learning model 130 is a deep convolutional neural network that is configured to receive the fundus image 150 and to process the fundus image 150 to generate a model output that characterizes a particular aspect of the patient's health.

The convolutional neural network illustrated in FIG. 2B is a simplified example of a deep convolutional neural network and includes a set of convolutional neural network layers 162, followed by a set of fully connected layers 164, and an output layer 166. It will be understood that, in practice, a deep convolutional neural network may include other types of neural network layers, e.g., pooling layers, normalization layers, and so on, and may be arranged in various configurations, e.g., as multiple modules, multiple subnetworks, and so on.

During the processing of the fundus image 150 by the convolutional neural network, the output layer 166 receives an output generated by the last fully connected layer in the set of fully connected layers 164 and generates the model output for the fundus image 150. In the example of FIG. 2B, the model output is a set of scores 170, with each score being generated by a corresponding node in the output layer 166. As will be described in more detail below, in some cases, the set of scores 170 are specific to particular medical condition. In some other cases, the each score in the set of scores 170 is a prediction of the risk of a respective health event occurring in the future. In yet other cases, the scores in the set of scores 170 characterize the overall health of the patient.

Once the set of scores 170 have been generated, the fundus image analysis system generates patient health analysis data that characterizes an aspect of the patient's health from the scores 170 and provides the health analysis data for presentation to the user in a user interface, e.g., on a user computer of the patient or on a computer of a medical professional, stores the health analysis data for future use, or provides the health analysis data for use for some other immediate purpose.

Figure 3:
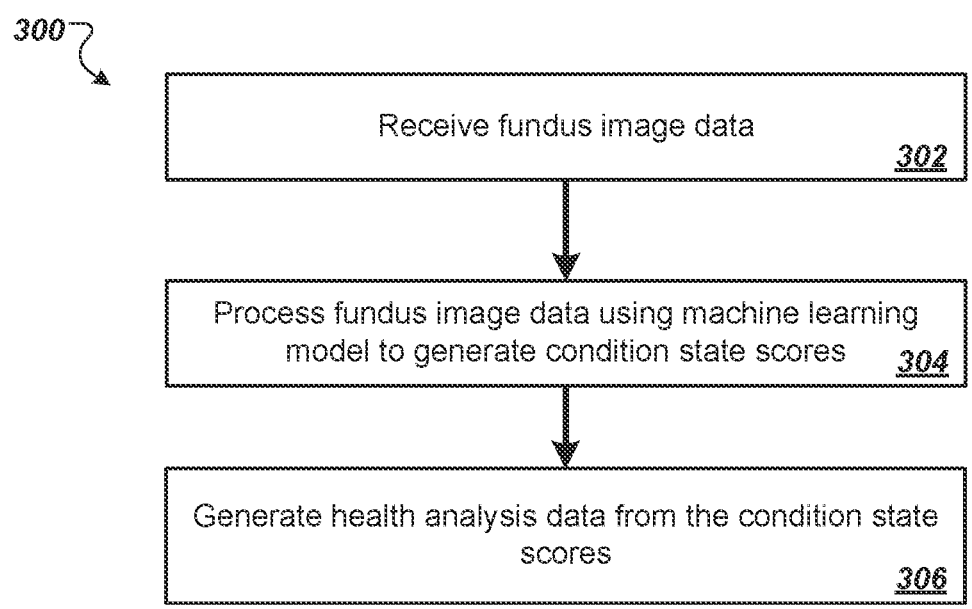
FIG. 3 is a flow diagram of an example process for generating health analysis data that is specific to a particular medical condition.

FIG. 3 is a flow diagram of an example process 300 for generating health analysis data that is specific to a particular medical condition. For convenience, the process 300 will be described as being performed by a system of one or more computers located in one or more locations. For example, a fundus image analysis system, e.g., the fundus image analysis system 100 of FIG. 1, appropriately programmed, can perform the process 300.

The system receives input fundus image data and, optionally, other patient data (step 302).

The system processes the input fundus image data and, optionally, the other patient data using a fundus image processing machine learning model to generate a set of condition state scores (step 304).

Generally, the set of condition state scores are specific to a particular medical condition that the system has been configured to analyze.

In some implementations, the medical condition is a particular eye-related condition.

For example, the particular eye-related condition may be glaucoma. Generally, glaucoma is a condition in which the optic nerve is damaged, which can result in blindness.

As another example, the particular eye-related condition may be age-related macular degeneration. Generally, age-related macular degeneration is a condition in which the macula, an area near the center of the retina, has deteriorated, which may cause partial or total vision loss.

As another example, the particular eye-related condition may be retinal detachment. Generally, retinal detachment is a disorder in which the retina detaches either partially or completely from its underlying layer of support tissue.

As yet another example, the particular eye-related condition may be ocular occlusions. Generally, an ocular occlusion is the blockage or closing of a blood vessel that carries blood to or from some portion of the eye, e.g., to or from the retina.

In some other implementations, the specific condition is not an eye-related condition but is instead a neurodegenerative condition, e.g., Parkinson's or Alzheimer's, or another condition that can effectively be analyzed using fundus imagery.

In some implementations, the set of condition state scores includes a single score that represents a likelihood that the patient has the medical condition.

For example, in the case of glaucoma, the single score may represent a likelihood that the patient has glaucoma.

As another example, in the case of age-related macular degeneration, the single score may represent a likelihood that the patient has age-related macular degeneration.

As another example, in the case of retinal detachment, the single score may represent a likelihood that the patient has retinal detachment.

As another example, in the case of ocular occlusions, the single score may represent a likelihood that the patient has one or more ocular occlusions.

As another example, in the case of neurodegenerative conditions, the single score may represent a likelihood that the patient has the neurodegenerative condition e.g., Parkinson's or Alzheimer's.

In some other implementations, the set of condition state scores includes a respective score for each of multiple possible levels of the medical condition, with each condition score representing a likelihood that the corresponding level is current level of the condition for the patient.

For example, in the case of glaucoma, the set of scores may include a score for no glaucoma, mild or early-stage glaucoma, moderate-stage glaucoma, severe-stage glaucoma, and, optionally, an indeterminate or unspecified stage.

As another example, in the case of age-related macular degeneration, the set of scores may include a score for no macular degeneration, early-stage macular degeneration, intermediate macular degeneration, advanced macular degeneration, and, optionally, an indeterminate or unspecified stage.

As another example, in the case of retinal detachment, the set of scores may include a score for no retinal detachment, initial retinal detachment, i.e., only retinal tears or retinal breaks, advanced retinal detachment, and, optionally, an indeterminate or unspecified stage.

As another example, in the case of ocular occlusions, the set of scores may include a score for no ocular occlusions, minor ocular occlusions, severe ocular occlusions, and, optionally, an indeterminate or unspecified stage.

As another example, in the case of neurodegenerative conditions, the set of scores may include a score for not having the neurodegenerative condition, a score for each of multiple stages of the neurodegenerative condition, and, optionally, an indeterminate or unspecified stage.

The system generates health analysis data from the condition state scores (step 306). For example, the system can generate health analysis data that identifies the likelihood that the patient has the medical condition or identifies one or more condition levels that have the highest condition state scores.

Figure 4:
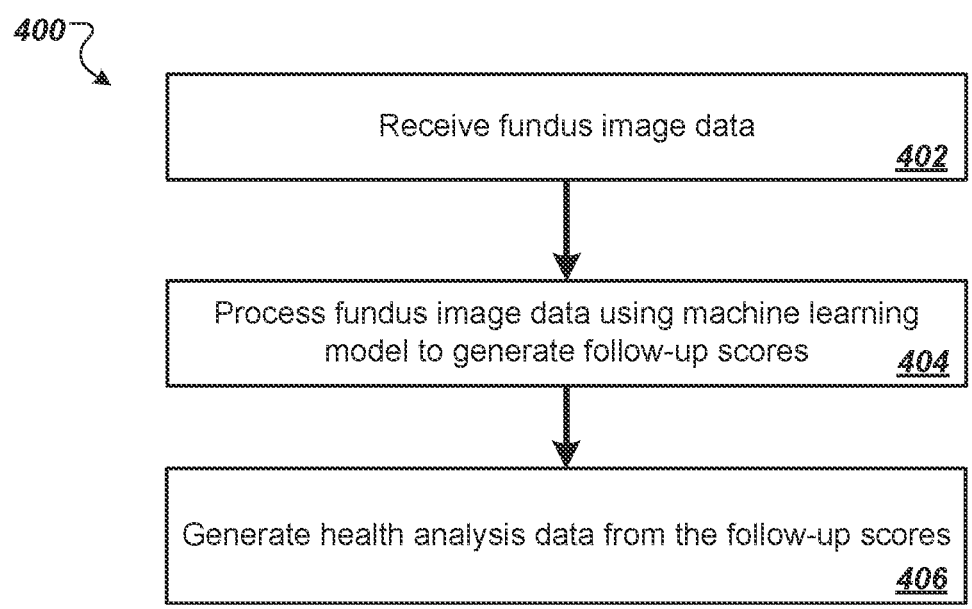
FIG. 4 is a flow diagram of an example process for generating health analysis data that identifies patient follow-up actions.

FIG. 4 is a flow diagram of an example process 400 for generating health analysis data that identifies patient follow-up actions. For convenience, the process 400 will be described as being performed by a system of one or more computers located in one or more locations. For example, a fundus image analysis system, e.g., the fundus image analysis system 100 of FIG. 1, appropriately programmed, can perform the process 400.

The system receives input fundus image data and, optionally, other patient data (step 402).

The system processes the input fundus image data and, optionally, the other patient data using a fundus image processing machine learning model to generate a set of follow-up scores (step 404).

The set of follow-up scores includes a respective score for each of multiple possible follow-up actions that can be taken by the patient to treat a particular medical condition. For example, the set of possible follow-up actions may include performing a re-screening at a future time, visiting a doctor at a future time, and visiting a doctor immediately. Each follow-up score represents a likelihood that the corresponding follow-up action is the proper action to be taken to effectively treat the medical condition.

The system generates health analysis data from the follow-up scores (step 406). For example, the system can generate health analysis data that recommends that the patient take the follow-up action that has the highest follow-up score.

Figure 5:
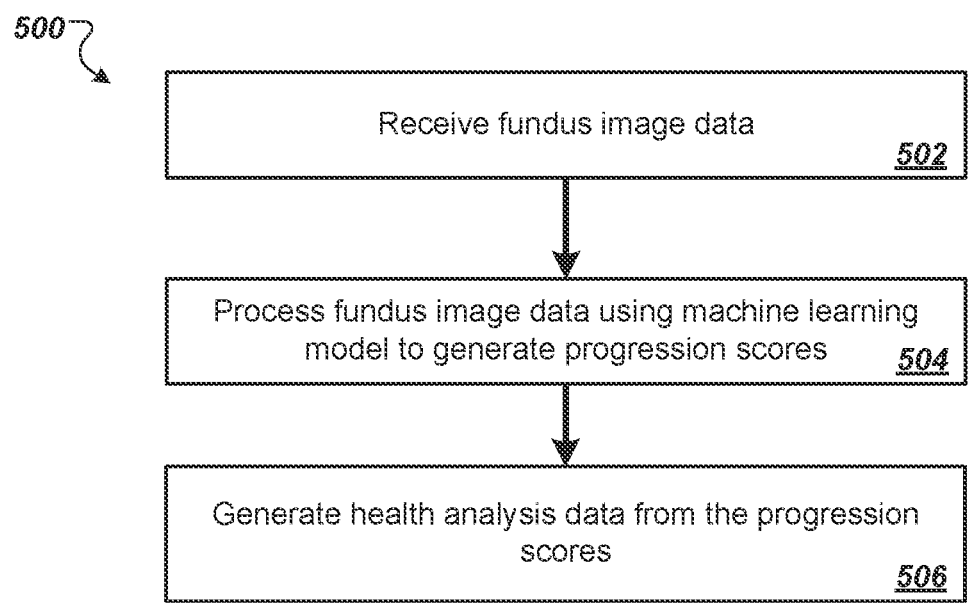
FIG. 5 is a flow diagram of an example process for generating health analysis data that predicts the likely progression of a medical condition.

FIG. 5 is a flow diagram of an example process 500 for generating health analysis data that predicts the likely progression of a medical condition. For convenience, the process 500 will be described as being performed by a system of one or more computers located in one or more locations. For example, a fundus image analysis system, e.g., the fundus image analysis system 100 of FIG. 1, appropriately programmed, can perform the process 500.

The system receives input fundus image data and, optionally, other patient data (step 502).

The system processes the input fundus image data and, optionally, the other patient data using a fundus image processing machine learning model to generate a set of progression scores (step 504). The set of progression scores are specific to a particular medical condition that the system has been configured to analyze. The set of condition state scores includes a respective score for each of multiple possible levels of the medical condition, with each condition score representing a likelihood that the corresponding level will be the level of the condition for the patient at a predetermined future time, e.g., in 6 months, in 1 year, or in 5 years.

For example, in the case of glaucoma, the set of scores may include a score for no glaucoma, mild or early-stage glaucoma, moderate-stage glaucoma, and severe-stage glaucoma, with the score for each stage representing the likelihood that the corresponding stage will be the stage of glaucoma for the patient at the future time.

As another example, in the case of age-related macular degeneration, the set of scores may include a score for no macular degeneration, early-stage macular degeneration, intermediate-stage macular degeneration, and advanced-stage macular degeneration, and, optionally, with the score for each stage representing the likelihood that the corresponding stage will be the stage of macular degeneration for the patient at the future time.

As another example, in the case of neurodegenerative conditions, the set of scores may include a score for not having the neurodegenerative condition and a score for each of multiple stages of the neurodegenerative condition, with the score for each stage representing the likelihood that the corresponding stage will be the stage of the condition for the patient at the future time.

The system generates health analysis data from the progression scores (step 506). The health analysis data identifies the likely progression of the medical condition for the patient. For example, the system can generate health analysis data that identifies one or more of the possible condition levels and, for each possible condition level, the likelihood that the corresponding level will be the future level of the condition for the patient.

Figure 6:
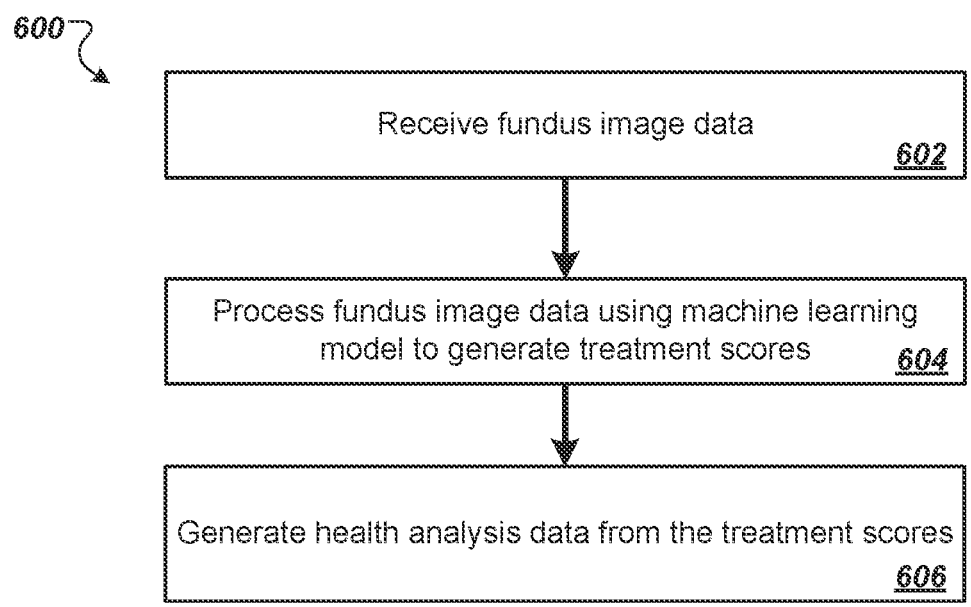
FIG. 6 is a flow diagram of an example process for generating health analysis data that predicts the proper treatment for a medical condition for a given patient.

FIG. 6 is a flow diagram of an example process 600 for generating health analysis data that predicts the proper treatment for a medical condition for a given patient. For convenience, the process 600 will be described as being performed by a system of one or more computers located in one or more locations. For example, a fundus image analysis system, e.g., the fundus image analysis system 100 of FIG. 1, appropriately programmed, can perform the process 600.

The system receives input fundus image data and, optionally, other patient data (step 602).

The system processes the input fundus image data and, optionally, the other patient data using a fundus image processing machine learning model to generate a set of treatment scores (step 604).

The set of treatment scores include a respective score for each of multiple possible treatments for a given medical condition, with each treatment score representing a likelihood that the corresponding treatment is the most effective treatment for the condition for the current patient.

For example, the set of treatment scores can include a respective score for each of multiple medications that can be prescribed to a patient that has the medical condition.

As another example, the set of treatment scores can include a respective score for each of multiple treatment plans for a given medical condition, e.g., a respective score for one or more medical procedures and a score for rehabilitation without undergoing a procedure.

The system generates health analysis data from the progression scores (step 606). For example, the health analysis data can identify one or more of the highest-scoring treatments.

Figure 7:
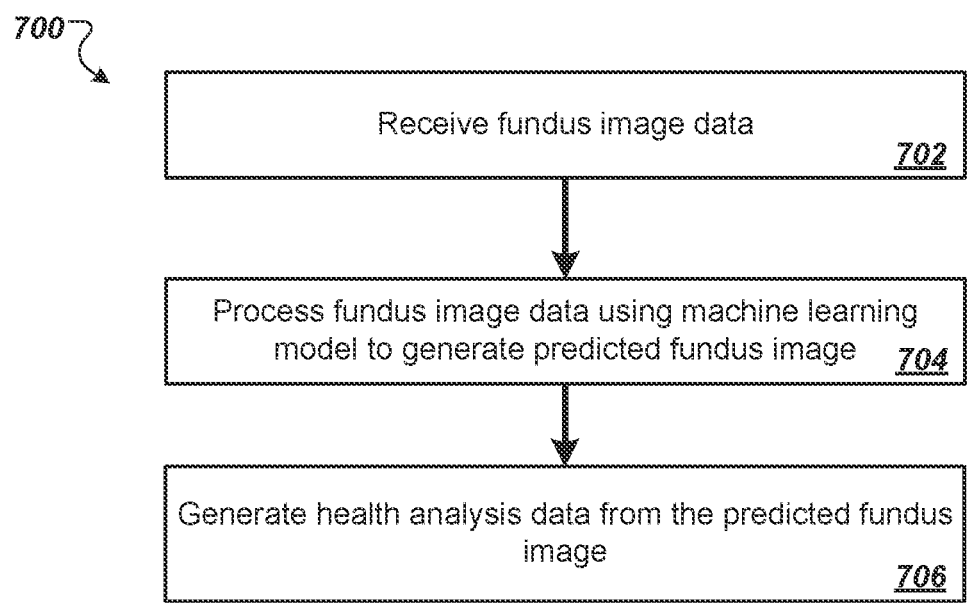
FIG. 7 is a flow diagram of an example process for generating health analysis data that includes a predicted fundus image.

FIG. 7 is a flow diagram of an example process 700 for generating health analysis data that includes a predicted fundus image. For convenience, the process 700 will be described as being performed by a system of one or more computers located in one or more locations. For example, a fundus image analysis system, e.g., the fundus image analysis system 100 of FIG. 1, appropriately programmed, can perform the process 700.

The system receives input fundus image data and, optionally, other patient data (step 702).

The system processes the input fundus image data and, optionally, the other patient data using a fundus image processing machine learning model to generate a predicted fundus image (step 704).

The predicted fundus image is an image of the fundus of the eye of the patient as it is predicted to look at a particular future time, e.g., in six months, in one year, or in five years.

For example, the fundus image processing machine learning model may be a convolutional neural network that is configured through training to predict, for each pixel in the input fundus image, the color of the pixel at the particular future time.

As another example, when the fundus image data includes a temporal sequence of fundus images, the fundus image processing machine learning model may be a recurrent neural network that is configured through training to, for each pixel in the most recent fundus image in the sequence, predict the color of the pixel at the particular future time.

The system can use the predicted color values for the pixels to generate the predicted fundus image.

The system generates health analysis data from the progression scores (step 706). For example, the health analysis data can include the predicted fundus image and, optionally, additional health analysis data.

Figure 8:
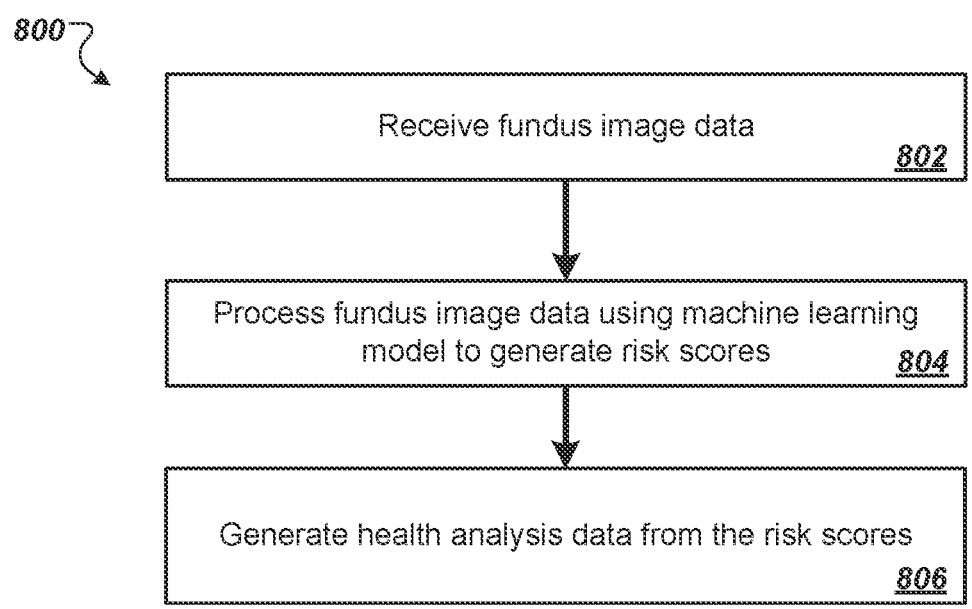
FIG. 8 is a flow diagram of an example process for generating health analysis data that predicts the risk of a health event occurring.

FIG. 8 is a flow diagram of an example process 800 for generating health analysis data that predicts the risk of a health event occurring. For convenience, the process 800 will be described as being performed by a system of one or more computers located in one or more locations. For example, a fundus image analysis system, e.g., the fundus image analysis system 100 of FIG. 1, appropriately programmed, can perform the process 800.

The system receives input fundus image data and, optionally, other patient data (step 802).

The system processes the input fundus image data and, optionally, the other patient data using a fundus image processing machine learning model to generate a set of risk scores (step 804).

In some implementations, the set of risk scores includes a single score that measures a particular kind of risk. For example, the score may measure a predicted cardiovascular risk of the patient, e.g., may be a predicted Framingham risk score that measures the 10-year cardiovascular risk of the patient.

In some other implementations, the set of risk scores may be specific to a particular undesirable health event.

For example, the undesirable health event may be a heart attack, a stroke, mortality, hospitalization, a fall, complications pre-operation or post-operation, and so on. In some of these implementations, the set of risk scores includes a single score that represents a likelihood of the undesirable health event occurring in the future, e.g., within a specified future time window. In others of these implementations, the set of risk scores includes a respective score for each of multiple risk levels, e.g., low, medium, and high, for the health event, with each risk score representing a likelihood that the corresponding risk level is the current risk level of the health event occurring.

In yet other implementations, the set of scores can include multiple scores, with each score corresponding to a respective undesirable health event and representing a likelihood that the corresponding undesirable health event will occur in the future, e.g., within a specified future time window.

The system generates health analysis data from the risk scores (step 806). For example, in implementations where the set of scores includes a single score, the health analysis data can identify the single score. As another example, where the set of scores includes multiple scores, the health analysis data can identify the highest-scoring risk level.

Figure 9:
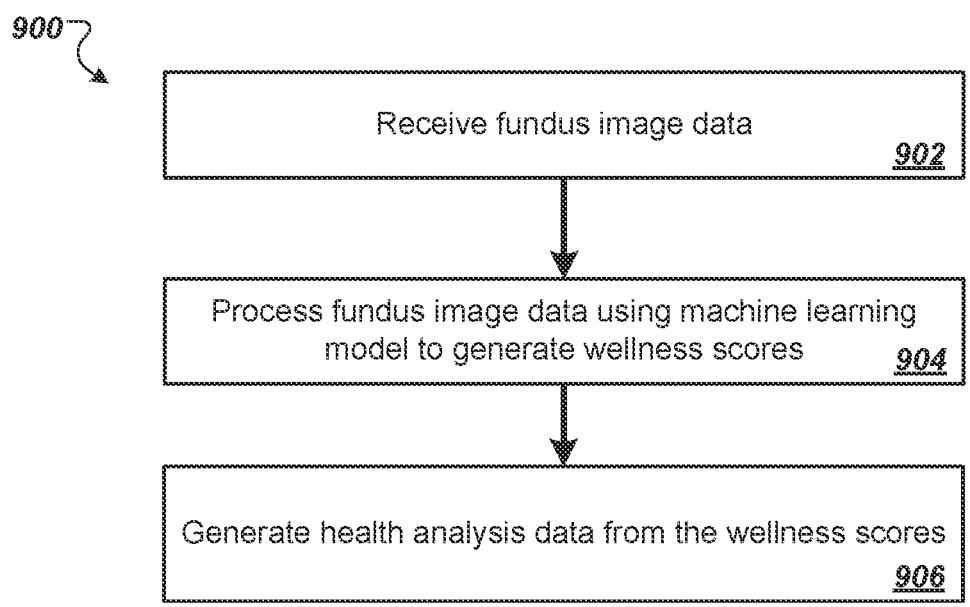
FIG. 9 is a flow diagram of an example process for generating health analysis data that characterizes the overall health of the patient.

FIG. 9 is a flow diagram of an example process 900 for generating health analysis data that characterizes the overall health of the patient. For convenience, the process 900 will be described as being performed by a system of one or more computers located in one or more locations. For example, a fundus image analysis system, e.g., the fundus image analysis system 100 of FIG. 1, appropriately programmed, can perform the process 900.

The system receives input fundus image data and, optionally, other patient data (step 902).

The system processes the input fundus image data and, optionally, the other patient data using a fundus image processing machine learning model to generate a set of wellness scores (step 904).

In some implementations, the set of wellness scores includes a single score that measures the overall health of the patient on a predetermined scale.

In some other implementations, the set of wellness scores may include a respective score for each of multiple wellness labels that each characterize the overall health of the patient. For example, the wellness labels may be "very healthy," "healthy," "somewhat unhealthy," and "very unhealthy." Each score represents a likelihood that the corresponding wellness label accurately characterizes the current health of the patient. Thus, for example the score for the wellness label "very healthy" represents the likelihood that the patient is very healthy, while the score for the "somewhat unhealthy" label represents the likelihood that the patient is somewhat unhealthy.

The system generates health analysis data from the risk scores (step 906). For example, in implementations where the set of scores includes a single score, the health analysis data can identify the single score. As another example, where the set of scores includes multiple scores, the health analysis data can identify the highest-scoring wellness label.

Figure 10:
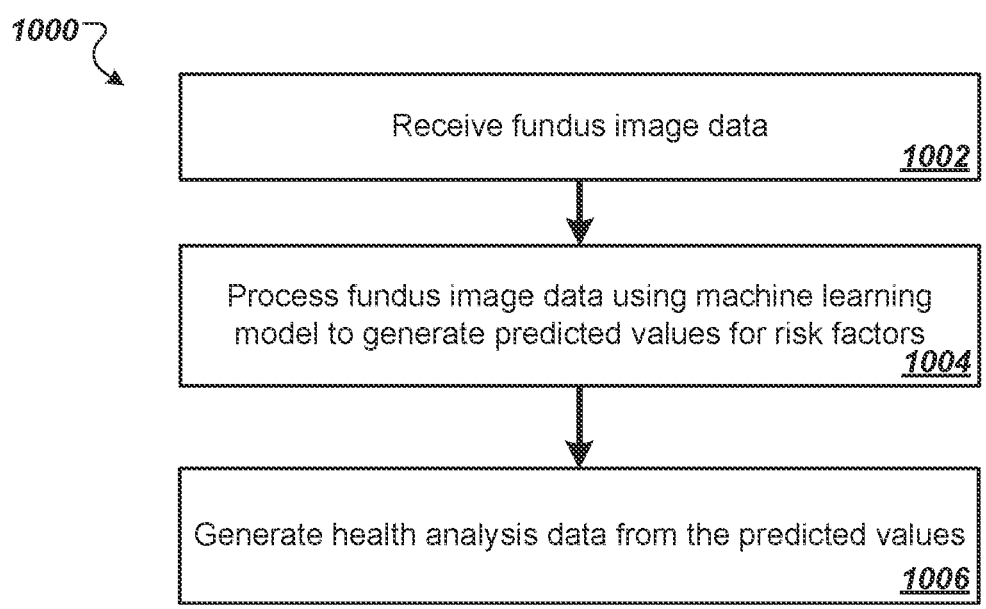
FIG. 10 is a flow diagram of an example process for generating health analysis data that includes predicted values for one or more risk factors.

FIG. 10 is a flow diagram of an example process 1000 for generating health analysis data that includes predicted values for one or more risk factors. For convenience, the process 1000 will be described as being performed by a system of one or more computers located in one or more locations. For example, a fundus image analysis system, e.g., the fundus image analysis system 100 of FIG. 1, appropriately programmed, can perform the process 1000.

The system receives input fundus image data that includes one or more fundus images (step 1002).

The system processes the input fundus image data using a fundus image processing machine learning model to generate a respective predicted value for each of one or more risk factors (step 1004).

Each of the risk factors is a factor that contributes to the risk of one of a particular set of health-related events happening to the patient. For example, when the risk is cardiovascular risk, the particular set of health-related events can be a health event that is classified as a major cardiovascular health event, e.g., myocardial infarction, heart failure, percutaneous cardiac intervention, coronary artery bypass grafting, malignant dysrhythmia, cardiac shock, implantable cardiac defibrillator, malignant dysrhythmia, cardiac-related mortality, and so on.

Continuing the example of cardiovascular risk, the risk factors can include one or more of: age, gender, body mass index, systolic blood pressure, diastolic blood pressure, a measure of HbA1c (glycated hemoglobin), or smoking status, i.e., whether or not the patient smokes cigarettes.

In some implementations, the system employs multiple machine learning models that each generate a predicted value for a different subset of the risk factors. For example, one model may generate predicted values for binary risk factors that can only take one of two values, e.g., smoking status and gender, while another model may generate predicted values for continuous risk factors that can take continuous values from some value range, e.g., age, body mass index, and blood pressure. Each of the two models may have similar architectures, but with different parameter values.

The system generates health analysis data from the predicted values (step 1006). For example, the health analysis data can identify each generated predicted value. In some cases, the system can use the predicted values to compute a measure of the particular risk and provide the computed measure of risk as part of the health analysis data. For example, the system can provide the predicted values as input to another machine learning model configured to predict the measure of risk or to a hard-coded formula to obtain the computed measure. For example, in the case of cardiovascular risk, the system can compute a Framingham risk score using the predicted values. Alternatively, the system can provide the predicted values as input to a machine learning model that has been trained to predict a risk measure based on values of risk factors.

Figure 11:
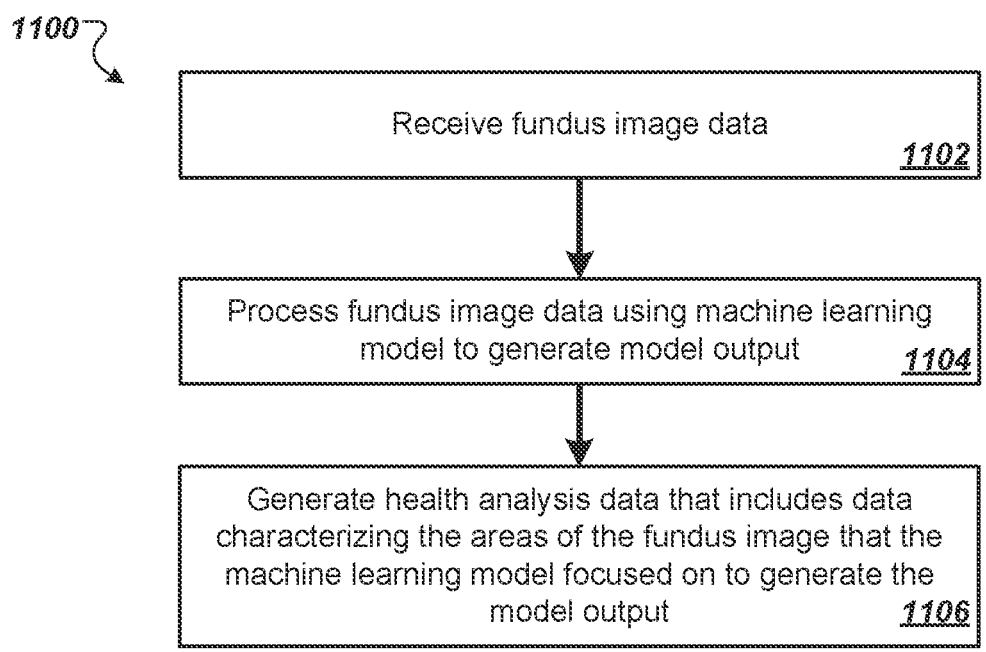
FIG. 11 is a flow diagram of an example process for generating health analysis data that includes data identifying locations in a fundus image that were focused on by the machine learning model when generating the model output.

FIG. 11 is a flow diagram of an example process 1100 for generating health analysis data that includes data identifying locations in a fundus image that were focused on by the machine learning model when generating the model output. For convenience, the process 1100 will be described as being performed by a system of one or more computers located in one or more locations. For example, a fundus image analysis system, e.g., the fundus image analysis system 100 of FIG. 1, appropriately programmed, can perform the process 1100.

The system receives input fundus image data and, optionally, other patient data (step 1102).

The system processes the input fundus image data and, optionally, the other patient data using a fundus image processing machine learning model to generate a model output (step 1104). The model output can be any of the model outputs described above with reference to FIGS. 2-10.

In particular, the machine leaning model is a model that includes one or more initial convolutional layers followed by an attention mechanism, which in turn is followed by one or more additional neural network layers.

The initial convolutional layers process each fundus image in the fundus image data to extract a respective feature vector for each of multiple regions in the fundus image.

The attention mechanism determines an attention weight for each of the regions in the fundus image and then attends to the feature vectors in accordance with the corresponding attention weights to generate an attention output. Generally, the attention mechanism attends to the feature vectors by computing a weighted sum or a weighted mean of the feature vectors, with the weight for each feature vector being the attention weight for the corresponding region. To determine the attention weights, the system can use any of a variety of attention schemes to determine the relevance of each of the feature vectors to generating the model output for the fundus image and then normalize the determined relevances to compute the attention weights. Example attention schemes include processing the feature vectors using one or more fully-connected layers to determine the relevance and determining the relevance of a given feature vector by computing a cosine similarity between the feature vector and a learned context vector. An example attention mechanism that can be adapted for use in the fundus image processing machine learning model is described in "Show, Attend and Tell: Neural Image Caption Generation with Visual Attention," Xu et al, available at https://arxiv.org/abs/1502.03044.

The additional neural network layers that follow the attention mechanism receive the attention output(s) for each of the fundus images and generate the model output from the attention output. For example, when the machine learning model is a recurrent neural network, the additional neural network layers include one or more recurrent layers. When the machine learning model is a convolutional neural network, the additional neural network layers can include convolutional neural network layers, fully-connected layers or other conventional feedforward neural network layers.

The system generates health analysis data from the risk scores (step 1106). In particular, as described above, the health analysis data characterizes the model output in a way that can be presented to a user of the system.

In addition, the health analysis data includes data characterizing the areas of the fundus image that the machine learning model focused on to generate the model output. In particular, the health analysis data include data identifying the attention weights assigned to the regions in the fundus image. For example, the system can generate an attention map that identifies, for each pixel in the fundus image, the attention weight assigned to the pixel, i.e., the attention weight for the region of the image that the pixel belongs to. For example, the attention map can be a heat map that represents the attention weights as colors. In some implementations, the system provides the attention map as an overlay of the corresponding fundus image.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term "database" is used broadly to refer to any collection of data: the data does not need to be structured in any particular way, or structured at all, and it can be stored on storage devices in one or more locations. Thus, for example, the index database can include multiple collections of data, each of which may be organized and accessed differently.

Similarly, in this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method comprising:
obtaining a model input comprising one or more fundus images, each fundus image being an image of a fundus of an eye of a patient;
processing the model input using a fundus image processing machine learning model, wherein the fundus image processing machine learning model is configured to process the model input comprising the one or more fundus images to generate a model output that characterizes the health of the patient with respect to one or more cardiovascular risk factors; and
processing the model output to generate health analysis data that characterizes an aspect of the health of the patient with respect to cardiovascular risk factors.

2. The method of claim 1, wherein the model input further comprises other patient data comprising ocular measurement data, patient demographic data, or both.

3. The method of claim 1, wherein the fundus image processing machine learning model is a feedforward machine learning model, and wherein the one or more fundus images comprise a single fundus image that captures a current state of the fundus of the eye of the patient.

4. The method of claim 1, wherein the fundus image processing machine learning model is a feedforward machine learning model, and wherein the one or more fundus images comprise a plurality of fundus images that each capture a different aspect of a current state of the fundus of the eye of the patient.

5. The method of claim 1 wherein the fundus image processing machine learning model is a recurrent machine learning model, and wherein the one or more fundus images comprise a temporal sequence of a plurality of fundus images that capture how the fundus of the patient has evolved over time.

6. The method of claim 1, wherein the model output comprises a respective predicted value for each of one or more cardiovascular risk factors.

7. The method of claim 6, wherein the one or more risk factors can comprise one or more of: age, gender, body mass index, systolic blood pressure, diastolic blood pressure, a measure of HbA1c, or smoking status.

8. The method of claim 6, wherein the one or more risk factors are used to compute a Framingham risk score.

9. The method of claim 1, wherein the fundus image processing machine learning model comprises an ensemble of machine learning models.

10. The method of claim 1 comprising employing multiple machine learning models that each generate a predicted value for a different subset of the cardiovascular risk factors.

11. The method of claim 1, wherein the fundus image processing machine learning model comprises an attention mechanism that is configured to:
receive a respective feature vector for each of a plurality of regions in the fundus image generated by one or more initial layers of the fundus image processing machine learning model,
compute a respective attention weight for each of the regions, and
generate an attention output by attending to the feature vectors in accordance with the attention weights for the regions in fundus image; and
wherein the health analysis data comprises data identifying the attention weights generated by the attention mechanism.

12. The method of claim 11, wherein the data identifying the attention weights is an attention map that specifies the attention weights for the regions in the fundus image.

13. A system comprising one or more computers and one or more storage devices storing instructions that when executed by the one or more computers cause the one or more computers to perform operations comprising:
obtaining a model input comprising one or more fundus images, each fundus image being an image of a fundus of an eye of a patient;
processing the model input using a fundus image processing machine learning model, wherein the fundus image processing machine learning model is configured to process the model input comprising the one or more fundus images to generate a model output that characterizes the health of the patient with respect to one or more cardiovascular risk factors; and
processing the model output to generate health analysis data that characterizes an aspect of the health of the patient with respect to cardiovascular risk factors.

14. The system of claim 13, wherein the model output comprises generating a respective predicted value for each of one or more risk factors.

15. One or more non-transitory computer-readable storage media encoded with instructions that when executed by one or more computers cause the one or more computers to perform to perform operations comprising:
obtaining a model input comprising one or more fundus images, each fundus image being an image of a fundus of an eye of a patient;
processing the model input using a fundus image processing machine learning model, wherein the fundus image processing machine learning model is configured to process the model input comprising the one or more fundus images to generate a model output that characterizes the health of the patient with respect to one or more cardiovascular risk factors; and processing the model output to generate health analysis data that characterizes an aspect of the health of the patient with respect to cardiovascular risk factors.

16. The one or more non-transitory computer-readable storage media of claim 15, wherein the model output comprises a respective predicted value for each of one or more cardiovascular risk factors.

17. The one or more non-transitory computer-readable storage media of claim 15, wherein the one or more risk factors can comprise one or more of: age, gender, body mass index, systolic blood pressure, diastolic blood pressure, a measure of HbAlc, or smoking status.

* * * * *